(12) United States Patent
Chu et al.

(10) Patent No.: US 12,268,369 B2
(45) Date of Patent: *Apr. 8, 2025

(54) MULTIPLE CHANNEL FLEXIBLE URETEROSCOPE

(71) Applicant: Boston Scientific Scimed, Inc., Maple Grove, MN (US)

(72) Inventors: Michael S. H. Chu, Brookline, MA (US); Mayur Patel, Framingham, MA (US); Sacha Tang, Lowell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 234 days.

This patent is subject to a terminal disclaimer.

(21) Appl. No.: 18/047,461

(22) Filed: Oct. 18, 2022

(65) Prior Publication Data
US 2023/0055911 A1    Feb. 23, 2023

Related U.S. Application Data

(63) Continuation of application No. 16/541,366, filed on Aug. 15, 2019, now Pat. No. 11,503,993.
(Continued)

(51) Int. Cl.
*A61B 1/00* (2006.01)
*A61B 1/307* (2006.01)
(Continued)

(52) U.S. Cl.
CPC ............ *A61B 1/307* (2013.01); *A61B 17/221* (2013.01); *A61B 1/015* (2013.01); *A61B 1/018* (2013.01); *A61B 2017/00477* (2013.01)

(58) Field of Classification Search
CPC ......... A61B 1/307; A61B 1/015; A61B 1/018; A61B 1/00137; A61B 1/0014; A61B 1/00089; A61B 2017/00477; A61B 17/221
See application file for complete search history.

(56) References Cited

U.S. PATENT DOCUMENTS 6,059,719 A * 5/2000 Yamamoto ....... A61B 17/00234
606/1
6,071,233 A   6/2000 Ishikawa et al.
(Continued)

OTHER PUBLICATIONS

Office Action in Chinese Application No. 201980054792.1, dated Jun. 17, 2024 (13 pages).
(Continued)

*Primary Examiner* — Timothy J Neal
(74) *Attorney, Agent, or Firm* — Bookoff McAndrews, PLLC

(57) ABSTRACT

A ureteroscope system includes a handle; an elongated shaft extends from the handle to a distal end and includes a working channel which is opened at the distal end; an external member extends from a proximal end to a distal end and is coupled to the shaft, the member includes a hub and a tube defining a first external channel; and a coupling mechanism defines first and second tubes and is coupled the distal end of the member to the distal end of the shaft. The first tube defines a first lumen and the second tube defines a second lumen which is sized and shaped to receive a distal end of the member. A proximal portion of the first tube is sized and shaped to be inserted into a distal portion of the shaft such that the first lumen is opened to the working channel.

20 Claims, 4 Drawing Sheets

Related U.S. Application Data

(60) Provisional application No. 62/735,721, filed on Sep. 24, 2018.

(51) Int. Cl.
*A61B 17/221* (2006.01)
*A61B 1/015* (2006.01)
*A61B 1/018* (2006.01)
*A61B 17/00* (2006.01)

(56) References Cited

U.S. PATENT DOCUMENTS

| | | |
|---|---|---|
| 6,921,362 B2 | 7/2005 | Ouchi |
| 8,702,695 B2 * | 4/2014 | Wallace ................. A61B 34/71 606/41 |
| 11,503,993 B2 * | 11/2022 | Chu ....................... A61B 1/307 |
| 2001/0053909 A1 * | 12/2001 | Nakada .............. A61B 1/00089 606/46 |
| 2003/0009085 A1 * | 1/2003 | Arai ................... A61B 1/00089 600/127 |
| 2004/0077927 A1 | 4/2004 | Ouchi |
| 2005/0228224 A1 | 10/2005 | Okada et al. |
| 2005/0234297 A1 | 10/2005 | Devierre et al. |
| 2008/0177135 A1 | 7/2008 | Muyari et al. |
| 2010/0016659 A1 | 1/2010 | Weitzner |
| 2012/0149979 A1 | 6/2012 | Mitelberg |
| 2016/0206178 A1 | 7/2016 | Lau |
| 2017/0112523 A1 | 4/2017 | Jagelski et al. |
| 2018/0000321 A1 * | 1/2018 | Wales ................ A61B 17/1285 |

OTHER PUBLICATIONS

Extended Search Report in European Application No. 24181525.7, dated Aug. 27, 2024 (7 pages).

* cited by examiner

MULTIPLE CHANNEL FLEXIBLE URETEROSCOPE

PRIORITY CLAIM

The present application is a Continuation of U.S. patent application Ser. No. 16/541,366 filed on Aug. 15, 2019, which claims priority to U.S. Provisional Patent Application Ser. No. 62/735,721 filed Sep. 24, 2018. The disclosures of the above application(s)/patent(s) are incorporated herewith by reference.

FIELD

The present disclosure relates generally to devices and related systems and methods for retrieving objects from within living bodies.

BACKGROUND

A single channel flexible ureteroscope often has a working channel with a small diameter—around 3.6 French (F) or about 0.47 inches. This small diameter limits the size or quantity of devices that can fit through the working channel, as well as the size of objects, such as stone debris, that can be extracted while a device remains within the working channel—i.e., a laser fiber used to fragment kidney stones with laser energy. Often, the laser fiber must be removed from the channel before suction is applied through the working channel to extract the stone fragments. The laser fiber must then be reintroduced into the working channel to continue fragmenting kidney stones.

Dual channel flexible ureteroscopes are available but are often not as efficient as a single channel flexible ureteroscopes. For example, dual-channel flexible ureteroscopes are typically less maneuverable and provide less visibility because additional space in the ureteroscope shaft is dedicated to the second channel. Furthermore, dual channel ureteroscopes are costly to obtain and maintain.

SUMMARY

The present disclosure relates to a ureteroscope system comprising a handle configured to remain outside the body, an elongated shaft extending from the handle to a distal end and including a working channel, the working channel being open at the distal end of the shaft, the shaft being configured to be inserted through a bodily lumen to a target surgical site, an external channel extending from a proximal end to a distal end and configured to be coupled to the elongated shaft, the external channel comprising a proximal hub and a tube extending distally from the hub and defining a second channel therein, the second channel having an internal diameter sized to receive a medical instrument therethrough, and a coupling mechanism defining a first tube and a second tube and configured to couple the distal end of the external channel to the distal end of the elongated shaft, the first tube defining a first lumen and the second tube defining a second lumen, the second lumen sized and shaped to receive a distal end of the external channel, a proximal portion of the first tube sized and shaped to be inserted into a distal portion of the elongated shaft such that the lumen is open to the working channel.

In an embodiment, the system further comprises an end cap coupled to a distal end of the elongated shaft, the end cap including a channel extending therethrough such that, when the end cap is coupled to the elongated shaft, the end cap channel is open to the working channel.

In an embodiment, a diameter of the end cap channel is substantially the same as an inner diameter of the working channel.

In an embodiment, the coupling mechanism includes an engagement feature configured to mate with an engagement feature on an inner wall of the end cap channel to lock the coupling mechanism to the end cap.

In an embodiment, the coupling mechanism is one of a barb or threading.

In an embodiment, the tube of the external channel has an inner diameter of approximately 3 French.

In an embodiment, the system further comprises a clip configured to couple the external channel to a proximal portion of the shaft, the clip including first and second slotted channels, each of the first and second slotted channels configured to receive one of the external channels and the shaft therethrough.

In an embodiment, the external channel is slidable relative to the clip.

The present disclosure also relates to a debris removal system comprising a scope assembly, comprising a handle configured to remain outside the body, an elongated shaft extending from the handle to a distal end and including a working channel, the working channel being open at the distal end of the shaft, the shaft being configured to be inserted through a bodily lumen to a target surgical site, an external channel extending from a proximal end to a distal end and configured to be coupled to the elongated shaft, the external channel comprising a proximal hub and a tube extending distally from the hub and defining a second channel therein, the second channel having an internal diameter sized to receive a medical instrument therethrough, and a coupling mechanism defining a first tube and a second tube and configured to couple the distal end of the external channel to the distal end of the elongated shaft, the first tube defining a first lumen and the second tube defining a second lumen, the first tube configured to be coupled to the elongated shaft and the second lumen configured to be coupled to the external channel, a medical device assembly configured to be coupled to the scope assembly via the hub of the external channel, the medical device assembly including a medical device configured to be inserted through the external channel to the target surgical site.

In an embodiment, the medical device assembly is a laser fiber assembly, the laser fiber assembly including a valve seal at a proximal end thereof configured to mate with a proximal end of the hub, sealing the laser fiber assembly to the scope assembly.

In an embodiment, the distal end of the elongated shaft is sized and shaped to be inserted into the first lumen of the first tube of the coupling mechanism and the distal end of the external channel is sized and shaped to be inserted into the second lumen of the second tube.

In an embodiment, the first and second tubes of the coupling mechanism are slotted clips, the first slotted clip being configured to snap over the distal end of the external channel and the second slotted clip being configured to snap over the distal end of the external channel.

In an embodiment, the system further comprises an end cap coupled to a distal end of the elongated shaft, the end cap including a channel extending therethrough such that, when the end cap is coupled to the elongated shaft, the end cap channel is open to the working channel.

In an embodiment, the system further comprises a clip configured to couple the external channel to a proximal portion of the shaft, the clip including first and second slotted channels, each of the first and second slotted channels configured to receive one of the external channels and the shaft therethrough.

In an embodiment, the system further comprises a vacuum source connected to the working channel via the handle and configured to apply suction through the working channel to vacuum debris from the target surgical site through the working channel.

The present disclosure also relates to a method for removing debris from a target surgical site, comprising inserting a distal portion of a scope assembly into a target lumen, the distal portion of the scope assembly including: an elongated shaft extending from the handle to a distal end and including a working channel, the working channel being open at the distal end of the shaft, the shaft being configured to be inserted through a bodily lumen to a target surgical site, an external channel extending from a proximal end to a distal end and configured to be coupled to the elongated shaft, the external channel comprising a proximal hub and a tube extending distally from the hub and defining a second channel therein, the second channel having an internal diameter sized to receive a medical instrument therethrough, and a coupling mechanism defining a first tube and a second tube and configured to couple the distal end of the external channel to the distal end of the elongated shaft, the first tube defining a first lumen and the second tube defining a second lumen, the second lumen sized and shaped to receive a distal end of the external channel, a proximal portion of the first tube sized and shaped to be inserted into a distal portion of the elongated shaft such that the lumen is open to the working channel, inserting a medical device through the external channel until a distal end of the medical device enters the target surgical site, the medical device configured to break up a debris within the target surgical site, and vacuuming the debris from the target surgical site through the working channel via a vacuum pump fluidly connected to the elongated shaft.

In an embodiment, the method further comprises inserting a guide wire into a body lumen to the target surgical site and guiding the distal portion of the scope assembly, via the guide wire, to the target surgical site.

In an embodiment, the medical device is a is a laser fiber assembly, the laser fiber assembly including a valve seal at a proximal end thereof configured to mate with a proximal end of the hub, sealing the laser fiber assembly to the scope assembly.

In an embodiment, the method further comprises an end cap coupled to a distal end of the elongated shaft, the end cap including a channel extending therethrough such that, when the end cap is coupled to the elongated shaft, the end cap channel is open to the working channel.

In an embodiment, the method further comprises injecting fluid through the external channel via a fluid source to flush out the target surgical site.

The present disclosure also relates to a ureteroscope system comprising a handle configured to remain outside the body, an elongated shaft extending from the handle to a distal end and including a working channel, the working channel being open at the distal end of the shaft, the shaft being configured to be inserted through a bodily lumen to a target surgical site, an external channel extending from a proximal end to a distal end and configured to be coupled to the elongated shaft, the external channel comprising a proximal hub and a tube extending distally from the hub and defining second and third channels therein, the second and third channels each having an internal diameter sized to receive a medical instrument therethrough, and a coupling mechanism defining a first tube and a second tube and configured to couple the distal end of the external channel to the distal end of the elongated shaft, the first tube defining a first lumen and the second tube defining a second lumen, the second lumen sized and shaped to receive a distal end of the external channel, a proximal portion of the first tube sized and shaped to be inserted into a distal portion of the elongated shaft such that the lumen is open to the working channel.

In an embodiment, the second tube has a substantially oval inner profile configured to match a substantially oval outer profile of the external channel.

In an embodiment, the second channel of the external channel is sized and shaped to receive a laser fiber and the third channel of the external channel is sized and shaped to receive a retrieval basket.

BRIEF DESCRIPTION

DETAILED DESCRIPTION

Figure 1:
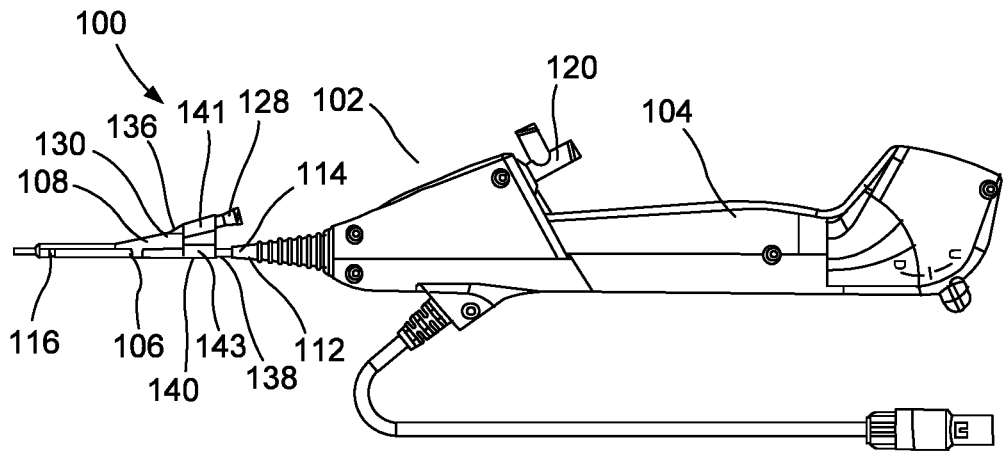
FIG. 1 shows a side view of a ureteroscope system according to an exemplary embodiment of the present disclosure.

The present disclosure may be further understood with reference to the appended drawings and the following description, wherein like elements are referred to with the same reference numerals. The present disclosure relates to ureteroscope devices and methods for breaking up and extracting objects from within a living body. Specifically, the present disclosure relates to a multiple channel flexible ureteroscope with both an internal and at least one external working channel. In some embodiments, the external channel(s) can be coupled or removably coupled to an existing flexible single channel ureteroscope. In other embodiments, the external channel(s) as well as one or more accessories may be coupled to a disposable or reusable ureteroscope. The accessories, in some embodiments may be an elongated medical device such as, for example, a laser fiber, a retrieval device, a guidewire, an injection catheter, a drainage catheter, a dilation balloon catheter, etc., or any combination thereof. It should be noted that the terms "proximal" and "distal", as used herein, are intended to refer to a direction toward (proximal) and away from (distal) a user of the device (e.g. physician).

FIG. 1 depicts a ureteroscope system 100 according to an exemplary embodiment of the present disclosure. The system 100 comprises an external channel 108 and a scope assembly 102 including a handle 104, which remains outside of a living body, and a shaft 106. The shaft 106 and external channel 108 provide access into a bodily lumen (e.g., along a tortuous path through a natural body lumen accessed via a naturally occurring body orifice). The scope assembly 102 may be a ureteroscope (e.g., Litho Vue™ Single-Use Digital Flexible Ureteroscope by Boston Scientific Corp.), an endoscope, a hysteroscope, a bronchoscope, a cystoscope, or any other similar device.

Figure 2:
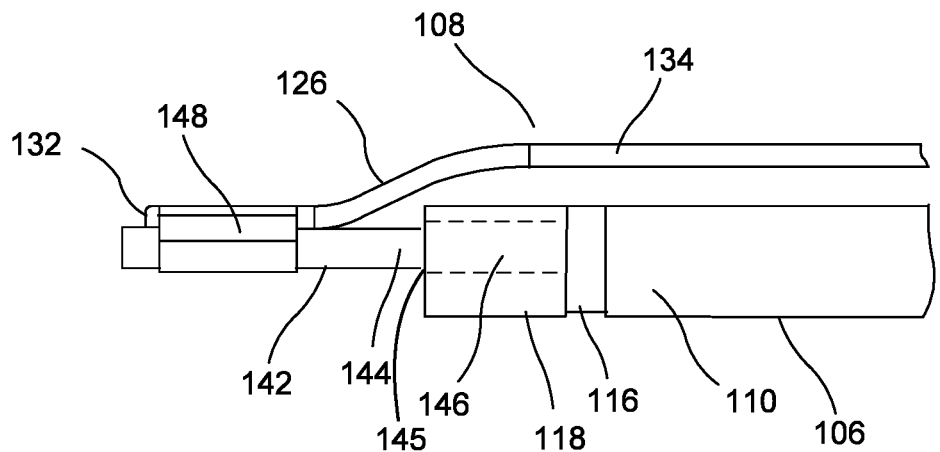
FIG. 2 shows an enlarged side view of a distal portion of the ureteroscope system of FIG. 1.
Figure 3:
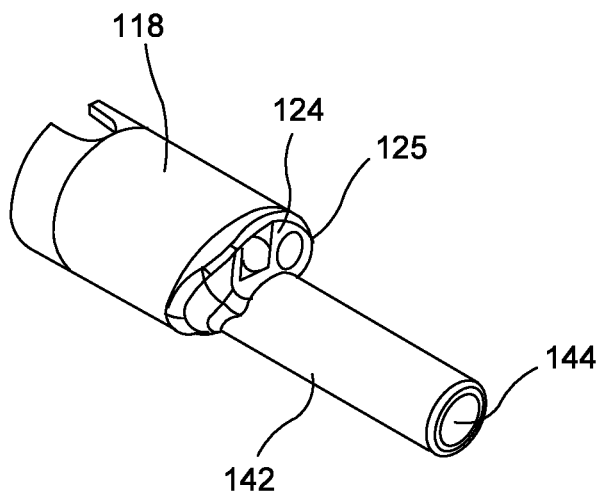
FIG. 3 shows a perspective view of an end cap of the ureteroscope of FIG. 1 according to a first exemplary embodiment.

In an exemplary embodiment shown in FIGS. 1-2, the scope assembly 102 such as, for example, a ureteroscope, applies vacuum pressure to a target cavity to draw debris, such as a kidney stone fragments or dust, from the target cavity into the scope assembly 102 for withdrawal from the body. The scope assembly 102 includes a scope shaft 106 sized and shaped to be inserted through a body lumen to a target cavity, as noted above. The shaft 106 has an inner diameter defining a working channel 110. In an exemplary embodiment, the working channel 110 has a diameter of 3.6 F, with the shaft 106 having an outer diameter of approximately 9.5 F such that the shaft 106 can navigate small lumens within the human body as would be understood by those skilled in the art. The shaft 106 extends from a proximal end 112, coupled to a distal end 114 of the handle 104, to a distal end 116, coupled to an end cap 118, as will be described in further detail below. As shown in FIG. 1, the scope assembly 102 may be connected to a vacuum pump (not shown) via a supply line (i.e., tubing). The tubing (not shown) may be coupled to a T-connector 120 in fluid communication, through the handle 104, with the working channel 110. Thus, the vacuum pump provides a source of vacuum pressure through the tubing and the working channel 110 of the shaft 106 to the target cavity to a target site within the living body at which a distal end of the shaft 106 is positioned. In an exemplary embodiment, the scope assembly 102 may include at least one sensor incorporated therein. For example, in one embodiment, the scope 106 includes a camera 124 for visualizing the target lumen or cavity into which the shaft 106 is inserted. The scope assembly 102 according to this embodiment also includes a light source 125, as shown in FIG. 3, for illuminating the body cavity. The handle 104, in an embodiment, allows the user to control the vacuum pump and/or the sensors via on/off switches. For example, the handle 104 may include a vacuum on/off button (not shown) such that the user has discretion to turn the vacuum on when debris, fluid, etc. is within the target cavity but can turn the vacuum off when suction is unnecessary.

The external channel 108, as shown in FIG. 1, includes an elongated tube 126 and a proximal hub 128. The elongated tube 126 extends from a proximal end 130 coupled, in this embodiment, to a distal end of the hub 130 to a distal end 132 coupled to the end cap 118. The tube 126 may be made of a polymer such as, for example, polyimide, PTFE, nylon, PE, and, in this embodiment, is reinforced with a braid or a coil. The tube 126 defines a second channel 134 extending therethrough from the hub 128 to the distal end 132. The second channel 134 has an inner diameter of approximately 3 F or less to accommodate medical devices such as laser wires, etc., of approximately 3 F or less. In another embodiment, the second channel 134 may be sized and shaped to allow fluid flow from the hub 128 to the distal end 132. As can be seen in FIGS. 1-2, the second channel 134 of tube 126 is smaller than the working channel 110 of the shaft 106 to manage channel efficiency and to minimize the outer profile of the scope assembly 102. It will be understood by those skilled in the art, however, that the second channel 134 may be sized and shaped as desired to meet a specific need for different procedures. For example, the second channel 134 may be configured to be a flat or oval low-profile tube to accommodate a round laser fiber such that fluid may be injected in the clearance space between the laser fiber and the inner wall of the second channel 134. In another example, the second channel 134 may have a larger diameter, similar to the working channel 110, and can be used to evacuate debris or stone dust. In this embodiment, the second channel 134 is coupled to the vacuum pump 120 in lieu of the working channel 110.

The tube 126 is coupled to the hub 128 via a connector 136 at the proximal end of the tube 126. For example, in an embodiment, the connector 136 is a medical female luer. The hub 128 is substantially tubular, defining an internal lumen 135 in communication with the second channel 134, and is configured to fit within a clip 140. Specifically, the hub 128 is secured to a proximal portion 138 of the shaft 106 via the clip 140. The clip 140 includes first and second slotted channels 141, 143 configured to removably snap over the hub 128 and the shaft 106, respectively, so that the external channel 108 may be removed from the scope assembly 102 as necessary. An outer diameter of the hub 128 is sized so that the hub 128 is capable of sliding proximally or distally within the clip 140 along a longitudinal axis of the first slotted channel 141 to allow for length adjustments of the external channel 108 during distal deflection of the scope assembly 102. A proximal end of the hub 128, in one embodiment, is configured to receive a medical device such as a laser fiber. The hub 128 may also be connected to a fluid source to allow fluid flow in the clearance space between the laser fiber and the inner wall of the second channel 134. In another embodiment, however, the hub 128 may be connected to the vacuum pump 120 to provide suction through the second channel 134 for vacuuming debris from the target cavity.

It will be understood that while the clip 140 of the present embodiment is configured to be coupled to the shaft 106 and the hub 128, the clip 140 can be modified to connect the external channel 108 to the scope assembly 102, or any other component, in any desired manner. For example, in one embodiment, the clip 140 may be mounted on the handle 104, coupling the external channel 108 thereto. In another example, the clip 140 may be configured to couple the shaft 106 to a shaft of an accessory medical device. Furthermore, the slotted channels 141, 143 may be sized and shaped to receive any size shaft 106, external channel 108, etc. For example, in an embodiment, the first slotted channel 141 may be sized and shaped to accommodate two hubs rather than one.

Figure 4:
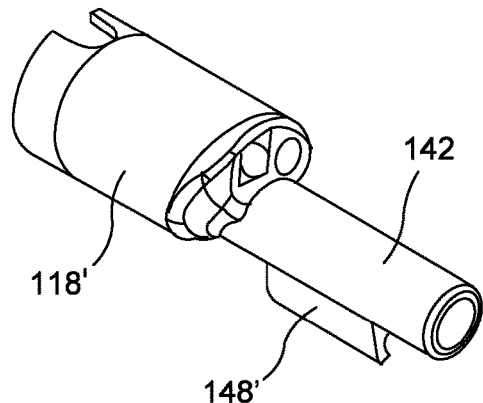
FIG. 4 shows a perspective view of an end cap of the ureteroscope of FIG. 1 according to a second exemplary embodiment.

The distal end 132 of the tube 126 is coupled to the shaft 106 via the end cap 118. The end cap 118 allows for a low-profile attachment of the tube 126 to the shaft 106. The distal end 132 is connected to the end cap 118 via a distal coupler or end cap tube 142, as shown in FIG. 2, defining an end cap tube channel 144. The end cap tube 142 is sized and shaped to be received within a lumen 146 of the end cap 118 to serve as an extension of the working channel 110. Specifically, an outer diameter of the end cap tube channel 144 is substantially equal to an inner diameter of the end cap lumen 146 while an inner diameter of the end cap tube channel 144 is substantially equal to an inner diameter of the working channel 110. Thus, the lumen 146 is in communication with the working channel 110 so that when the end cap tube 142 is inserted therein, the end cap tube channel 144 is open to the working channel 110. In another embodiment, the end cap tube 142 has external self-tapping threading on a proximal portion thereof configured to thread into an inner wall of the end cap lumen 146. In an embodiment, the end cap tube 142 includes a barb 145 or a taper at a proximal end thereof configured to engage an inner dimension of the end cap lumen 146, providing an interference fit between the two components. In another exemplary embodiment, the end cap tube 142 may be press-fitted, insert-molded or molded in one piece with the end cap 118. The tube 126, as shown in FIGS. 1-2, is connected to the end cap tube 142 via a connecting tube 148. The connecting tube 148 may be, for example, a heat shrink tube through which the distal end 132 of the tube 126 is inserted. As depicted in FIG. 4, the connecting tube 148 may be positioned anywhere on the external surface of the end cap tube 142 such as, for example, on the side of the end cap tube 142 opposing the hub 128. In another embodiment, the tube 126 may be glued to the connecting tube 148. In another exemplary embodiment, the tube 126 may be directly heat shrunk to a distal portion of the shaft 106 using a thin wall heat shrink tube in the range of 0.125 in. in diameter with a wall having a thickness of approximately 0.001 in.

When coupled to the end cap tube 142, a distal tip of the tube 126 may be set proximally of a distal tip of the end cap tube 142. Thus, the length D of the end cap tube 142 extending from the end cap 118 may be at the focal length of the camera 124 such that the distal tip of the end cap tube 142 is visible to the user in the field of view of the camera 124. In an embodiment, the end cap 118 and end cap tube 142 are formed of a clear or transparent polymer to allow for greater visibility by the camera 124. The end cap tube 142, in an embodiment, may also act as a nozzle to reach deep into a body cavity such as, for example, a calyx, to suction out or blow out stone debris. In another embodiment, the end cap tube 142 is capable of collapsing/retracting a non-sheathed self-expanding retrieval basket inserted therethrough.

Figure 5:
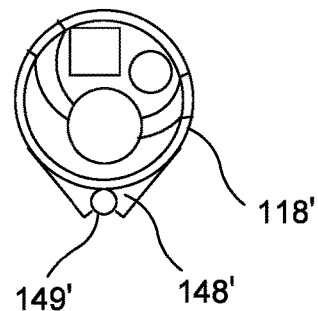
FIG. 5 shows a front view of an end cap of the ureteroscope of FIG. 1 according to a third exemplary embodiment.

FIGS. 4-5 depict another exemplary end cap 118'. In this embodiment, the end cap 118' includes a slotted clip 148' formed on an external wall thereof and sized and shaped to receive the distal end 132 of the tube 126. The tube 126 of the external channel 108 may be mounted or glued into a lumen 149' of the slotted clip 148' in lieu of an end cap tube. Such a configuration will result in a similar sized outer profile that is achieve by the end cap 118 and end cap tube 142 of the scope assembly 102.

Figure 6:
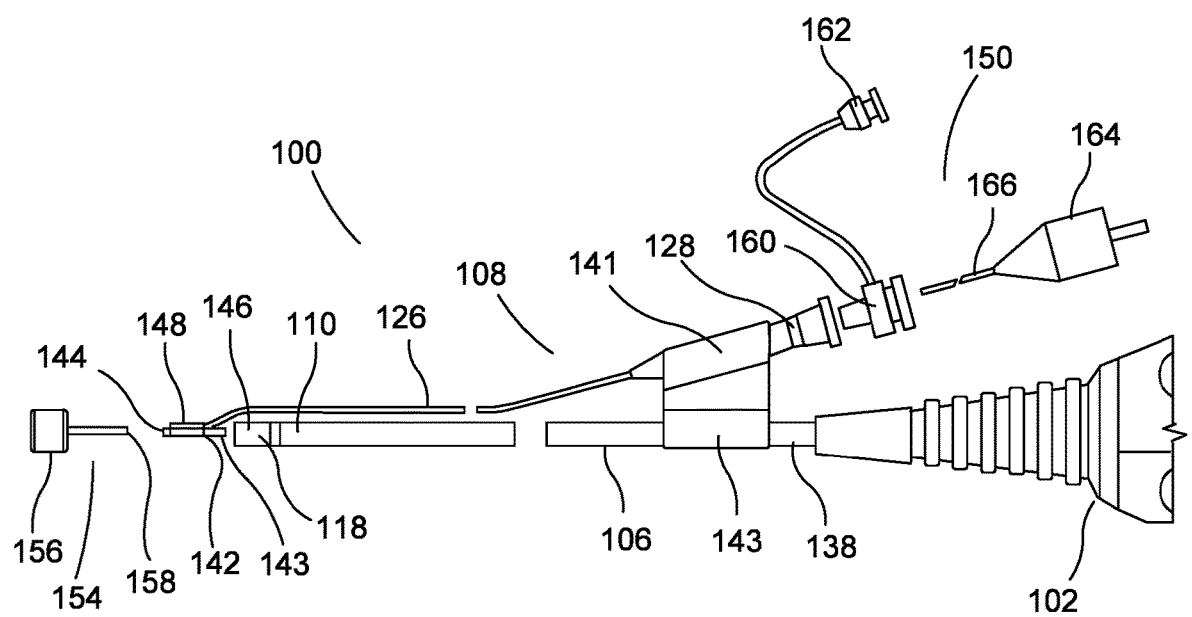
FIG. 6 shows a side view of a ureteroscope system with a laser fiber assembly according to an exemplary embodiment of the present disclosure.

FIG. 6 depicts an exemplary method of assembling the ureteroscope system 100 in which the system 100 uses a laser fiber assembly 150 capable of breaking down and evacuating stone debris simultaneously. The laser fiber assembly 150 includes a proximal seal fitting 160 such as a Touhy-Borst valve, a side port 162, a proximal plug connector 164 and a laser fiber 166. It will be understood that, although this embodiment describes the use of a laser fiber assembly 150, any medical device may be used such as, for example, a guidewire, a retrieval device, a cautery device, a needle device, etc. In a preferred embodiment, the external channel 108 is coupled to the scope assembly 102 by insertion of the proximal end of the end cap tube 142 into the distal tip of the end cap 118 such that the end cap tube channel 144 is in communication with the working channel 110 of the shaft 106. As noted previously, the tube 126 of the external channel 108 may be coupled to the end cap tube 142 via the connecting tube 148 (end cap tube 142 and connecting tube 148 may be pre-formed or pre-molded into a single piece). In an exemplary embodiment, the end cap tube 142 may be loaded into the end cap 118 using a loader tool 154. The loader tool 154 includes a handle 156 and a rod 158. The rod 158 is inserted into the end cap tube 142 to aid in pushing or rotating the end cap tube 142 in the proximal direction into the lumen 146 of the end cap 118. When the end cap tube 142 is pushed into the end cap 118 via the loader tool 154, the barb 145 engages the step (not shown) of the end cap lumen 146 to provide an interference fit between the end cap 118 and the end cap tube 142 and to prevent the end cap tube 142 from being withdrawn from the end cap 118. At this point, the channel 144 of the end cap tube 142 abuts against the working channel 110 with the diameters of the end cap tube 142 and working channel 110 matching to provide an internal transition between the two components. The loader tool 154 is then removed from the scope assembly 102, leaving the external channel 108 coupled to the scope assembly 102.

The hub 128 is subsequently attached to the proximal portion 138 of the shaft 106 via the clip 140. Specifically, the shaft 106 may be first clipped within the second slotted channel 143 of the clip and the hub 128 clipped into the first slotted channel 141 thereafter. However, it will be understood that the shaft 106 and hub 128 may be clipped to the slotted channels 141, 143 in any order. The laser fiber assembly 150 is connected to the hub 128 by inserting the Touhy-Borst valve 160 into the proximal end of the hub 128 to provide a proximal seal around the laser fiber 166 and the side port 162, allowing fluid communication from the Touhy-Borst valve 160 to the distal end of the tube 126. The laser fiber 166 may then be slidably inserted into the Touhy-Borst valve 160 until the plug connector 164 is positioned within the Touhy-Borst valve 160 providing a sealed connection between the scope assembly 102 and the laser fiber assembly 150. It should be noted that the external channel 108, because it is external to the shaft 106 of the scope assembly 102, has minimal effects in the deflection of the distal portion of the shaft 106. Furthermore, there is no change in the visibility of the visual image. Rather, the described means of coupling the tube 126 to the shaft 106 via the end cap tube 142 provides a secure and very low-profile connection.

An exemplary method for breaking up and removing debris or kidney stones from a body cavity includes inserting a guide wire or an 11/13 F access sheath into a body lumen to a target body cavity in, for example, the kidney. The shaft 106, with the external channel 108 attached thereto, is then inserted into the body and guided by the guide wire or access until the distal end 112 of the shaft 106 is positioned within the target cavity. The guide wire/access sheath is removed from the body. The laser fiber 166 is inserted into the hub 128 and advanced through the tube 126 until a distal end thereof extends past the distal end 132 of the tube 126. Inlet fluid can be injected/pumped from a fluid source attached to the side port 162. The inlet fluid is used to maintain a constant volume/pressure within the kidney as fluid and stone fragments are suctioned out. As the laser fiber 166 is fragmenting the kidney stones, the stone fragments are suctioned through the working channel 110 for removal. Fragmenting, fluid injection and suction may continue at the physician's discretion or until the kidney stone is removed in its entirety from the kidney.

Figure 7:
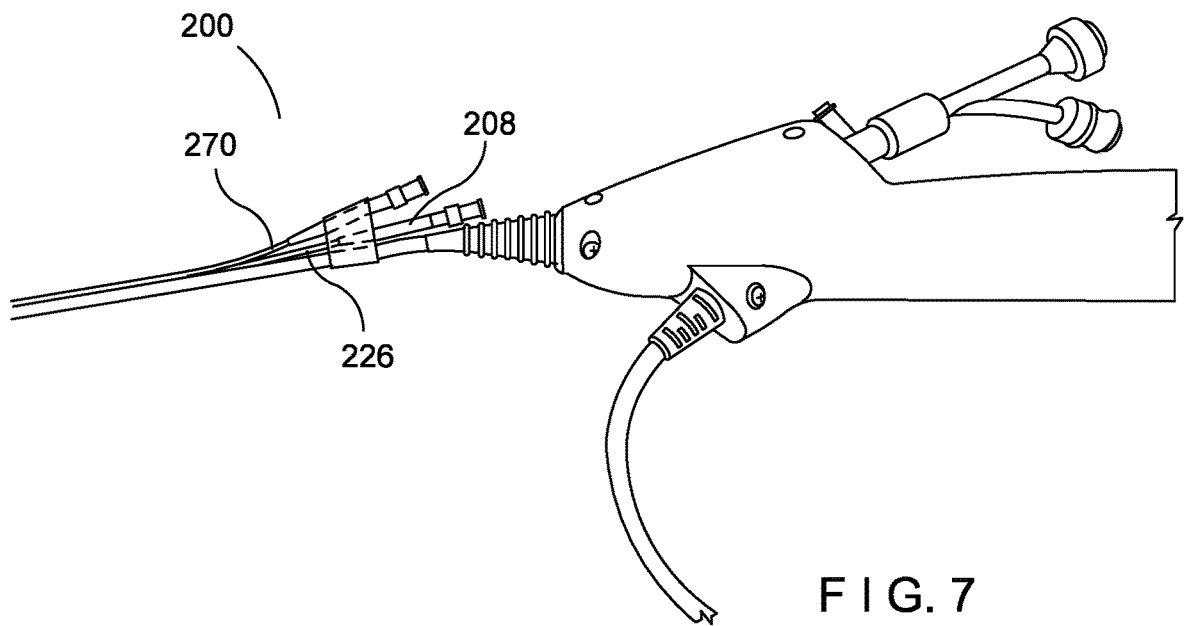
FIG. 7 shows a perspective view of a ureteroscope system according to a second exemplary embodiment of the present disclosure.
Figure 8:
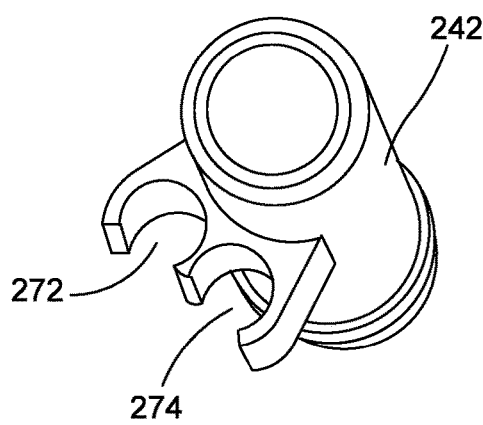
FIG. 8 shows perspective view of an end cap tube of the system of FIG. 7 according to a first exemplary embodiment.

As shown in FIGS. 7-8, a system 200 according to an exemplary embodiment of the present disclosure is substantially similar to the system 100, except as described herein. Specifically, the system 200 includes a second external channel 270 that can be used, for example, for injection/pumping of fluids into the kidney for a stone fragmenting procedure. In another example, the second external channel 270 may receive a retrieval basket to stabilize the kidney stone during fragmentation. As shown in FIG. 8, in one embodiment, the end cap tube 242 is molded with two slots or clips 272, 274. The tube 226 of the external channel 208 is glued into slot 272 while a tube of the second external channel 270 is glued to the slot 274. The end cap tube 242, in this embodiment, may be inserted, press-fitted, insert-molded or molded in one piece to the end cap 218.

Figure 9:
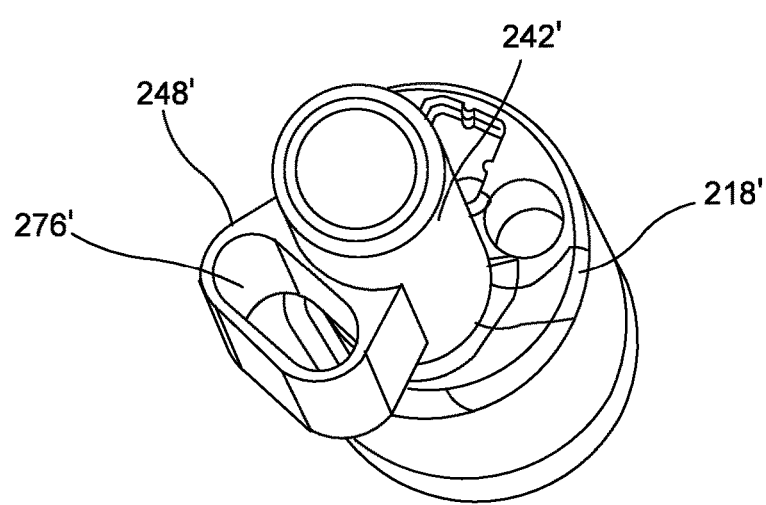
FIG. 9 shows a perspective view of an end cap and end cap tube of the system of FIG. 7 according to a second exemplary embodiment.

In another embodiment, shown in FIG. 9, the end cap tube 242' may include a connecting tube 248' with an oval shaped lumen 276' configured to receive a tube 226'. However, in this embodiment, the tube 226' may be a two-lumen extrusion with an oval outer profile matching the inner profile of the lumen 276'. Thus, the tube 226' may be received and glued within the end cap tube 242'. As with the previous embodiments, the end cap tube 242', in this embodiment, may be inserted, press-fitted, insert-molded or molded in one piece to the end cap 218'.

Figure 10:
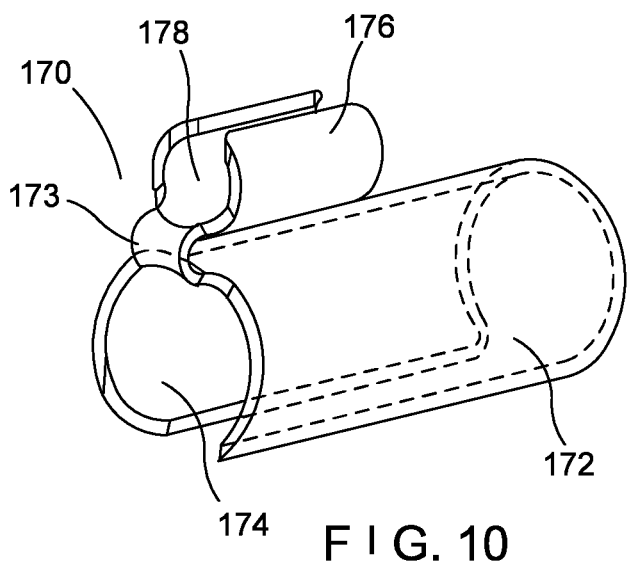
FIG. 10 shows a perspective view of a coupler of the system of FIG. 1 according to a first exemplary embodiment.

FIGS. 10-13 depict alternate means, in lieu of the end cap tube 142, for connecting the external channel 108 to the scope assembly 102. Turning to FIG. 10, a coupler 170 is substantially similar to the end cap tube 142, except as described herein. The coupler 170 is depicted including a first tube 172 defining a first channel 174 and a second tube 176 defining a second channel 178. The first and second tubes 172, 176 are connected by a distal connecting portion 173. As can be seen in the figure, the first tube 172 has a diameter that is greater than the dimeter of the second tube 176. Specifically, the outer diameter of the first tube 172 is substantially the same as the diameter of the end cap lumen 146 such that the first tube 172 can be slidably inserted therein. The outer diameter of the second tube 176 is substantially the same as the diameter of the second channel 134 of the tube 126 such that the second tube 176 can be slidably inserted therein, coupling the external channel 108 to the scope assembly 102. The distal connecting portion 173 extends from the first tube 172 in the end cap lumen 146 over distal abutting edges of the end cap 118 and the tube 126 to the second tube 176 in the second channel 178. In an exemplary embodiment, the first and second tubes 172, 176 may be glued in place within the end cap 118 and tube 126, respectively.

Figure 11:
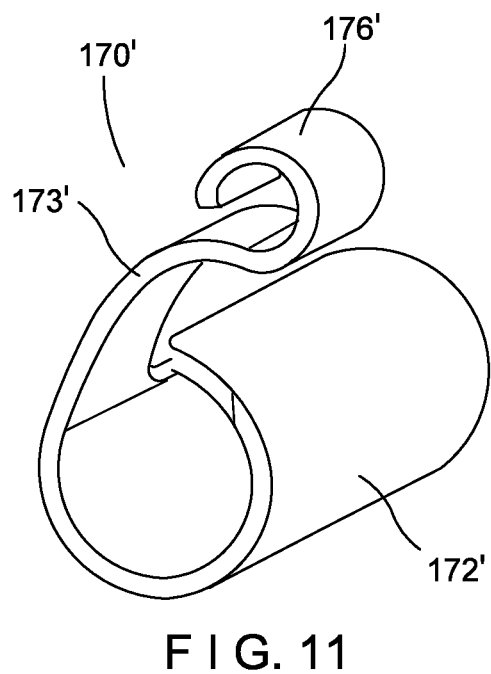
FIG. 11 shows a perspective view of a coupler of the system of FIG. 1 according to a second exemplary embodiment.

FIG. 11 depicts another exemplary embodiment of a coupler 170' that is substantially similar to coupler 170, except as described herein. Specifically, a connecting portion 173' of the coupler 170' extends laterally from the first tube 172' to the second tube 174' rather than distally. Thus, the coupler 170' may be manufactured using a single piece of, for example, thin sheet metal instead of molding a thin wall polymer part.

Figure 12:
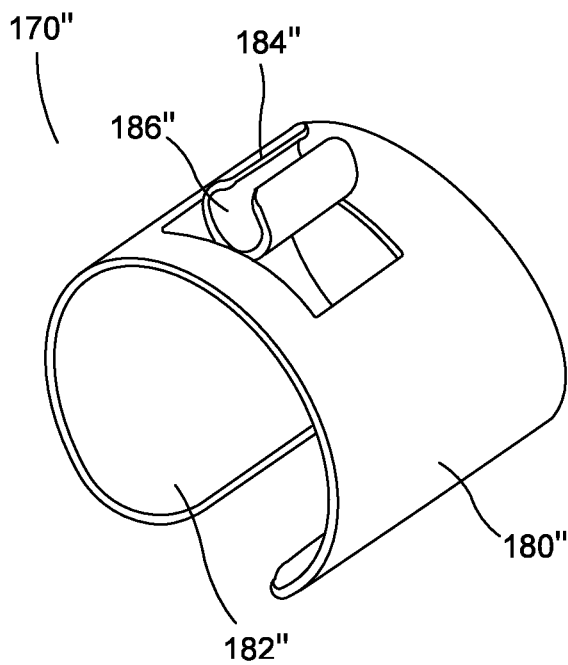
FIG. 12 shows a perspective view of a coupler of the system of FIG. 1 according to a third exemplary embodiment.

FIG. 12 depicts another exemplary embodiment of a coupler 170" that is substantially similar to couplers 170, 170', except as described herein. Specifically, the coupler 170" includes a first slotted clip portion 180" defining a first channel 182" and a second slotted clip portion 184" defining a second channel 186". The first slotted clip portion 180" is configured to snap over the outer diameter of the end cap 118 while the second slotted clip portion 184" is configured to snap over the outer diameter of the tube 126. In this embodiment, the end cap 118 may include at least one stop positioned on the external surface thereof to prevent the coupler 170" from sliding proximally or distally relative thereto.

Figure 13:
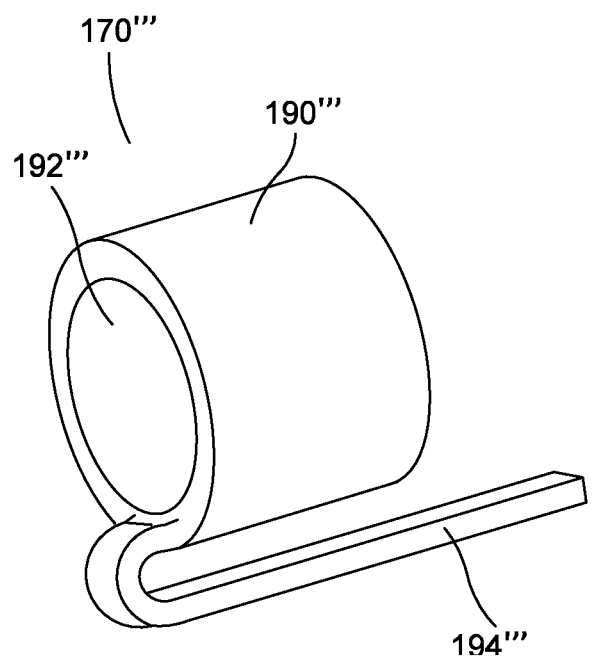
FIG. 13 shows a perspective view of a coupler of the system of FIG. 1 according to a fourth exemplary embodiment.

FIG. 13 depicts another exemplary embodiment of a coupler 170''' that is substantially similar to couplers 170, 170', 170", except as described herein. Specifically, the coupler 170''' includes a tube 190'''' defining a channel 192''' and a wire 194'''. The channel 192''' has a diameter that is substantially the same as the outer diameter of the tube 126 so that the tube 126 may be inserted thereinto. The wire 194''' is configured to be inserted into a hole (not shown) drilled into the end cap 118 to couple the external channel 108 to the scope assembly 102. The hole (not shown), in this embodiment, is separate from the end cap lumen 146 and working channel 110 of the shaft 106 such that the wire 194''' does not interfere with the functionality of either.

It will be appreciated by those skilled in the art that the current devices and methods are not limited to the disclosed embodiments. For example, the disclosed system 100 may be used in various other procedures such as, for example, hysteroscopies, cystoscopies, etc. Thus, the system 100 is not limited to use with a ureteroscope by may be used with other devices such as cystoscopes, hysteroscopes or any other device with a shaft inserted into a body channel/lumen/cavity.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiments disclosed, but rather, modifications are also covered within the scope of the present invention as defined by the appended claims.

What is claimed is:

1. A ureteroscope system, comprising:
  a handle configured to remain outside a body of a patient;
  an elongated shaft extending from the handle to a distal end and including a working channel, the working channel being open at the distal end of the elongated shaft, the elongated shaft being configured to be inserted through a bodily lumen to a target surgical site;
  an external member extending from a proximal end to a distal end and configured to be coupled to the elongated shaft, the external member comprising a proximal hub and a tube extending distally from the hub and defining a first external channel therein, the first external channel having an internal diameter sized to receive a medical instrument therethrough;
  a coupling mechanism configured to couple the distal end of the external member to the distal end of the elongated shaft, the coupling mechanism including a first lumen a proximal portion of which is sized and shaped to be inserted into a distal portion of the elongated shaft such that the first lumen is open to the working channel and wherein a second lumen of the coupling mechanism is sized and shaped to receive the distal end of the external member; and an end cap coupled to the distal end of the elongated shaft, the end cap including an end cap channel extending therethrough such that, when the end cap is coupled to the elongated shaft, the end cap channel is open to the working channel.

2. The system of claim 1, wherein the end cap is coupled to the distal end of the external member via a tube extending from the end cap.

3. The system of claim 1, wherein a diameter of the end cap channel is substantially the same as an inner diameter of the working channel.

4. The system of claim 1, wherein the coupling mechanism includes an engagement feature configured to mate with an engagement feature on an inner wall of the end cap channel to lock the coupling mechanism to the end cap.

5. The system of claim 4, wherein the engagement feature is one of a barb or threading.

6. The system of claim 1, wherein the tube of the first external channel has an inner diameter of approximately 3 French.

7. The system of claim 1, further comprising a clip configured to couple the first external channel to a proximal portion of the elongated shaft, the clip including first and second slotted channels, each of the first and second slotted channels being configured to receive the external member and the elongated shaft therethrough.

8. The system of claim 7, wherein the external member comprises a second external channel extending therethrough from the proximal end to the distal end of the external member.

9. A debris removal system, comprising:
a scope assembly, comprising:
a handle configured to remain outside a body of a patient;
an elongated shaft extending from the handle to a distal end and including a working channel, the working channel being open at the distal end of the elongated shaft, the elongated shaft being configured to be inserted through a bodily lumen to a target surgical site;
an external member extending from a proximal end to a distal end and configured to be coupled to the elongated shaft, the external member comprising a proximal hub and a tube extending distally from the hub and defining a first external channel therein;
a coupling mechanism configured to couple the distal end of the external member to the distal end of the elongated shaft, the coupling mechanism including a first lumen a proximal portion of which is sized and shaped to be inserted into a distal portion of the elongated shaft such that the first lumen is open to the working channel and wherein a second lumen of the coupling mechanism is sized and shaped to receive the distal end of the external member; and
an end cap coupled to the distal end of the elongated shaft, the end cap including an end cap channel extending therethrough such that, when the end cap is coupled to the elongated shaft, the end cap channel is open to the working channel; and
a medical device assembly configured to be coupled to the scope assembly via the hub of the first external channel, the medical device assembly including a medical device configured to be inserted through the first external channel to the target surgical site.

10. The system of claim 9, wherein the medical device assembly is a laser fiber assembly, the laser fiber assembly including a valve seal at a proximal end thereof configured to mate with a proximal end of the hub, sealing the laser fiber assembly to the scope assembly.

11. The system of claim 9, wherein the distal end of the external member is sized and shaped to be inserted into the second lumen.

12. The system of claim 9, wherein the first lumen extends through a first tube, the second lumen extends through a second tube, the second tube being a slotted clip configured to receive the distal end of the external member.

13. The system of claim 9, wherein the end cap is coupled to the distal end of the external member via a tube extending from the end cap.

14. The system of claim 9, further comprising a clip configured to couple the first external channel to a proximal portion of the elongated shaft, the clip including first and second slotted channels, each of the first and second slotted channels configured to receive one of the first external channel and the elongated shaft therethrough.

15. The system of claim 9, further comprising a vacuum source connected to the working channel via the handle and configured to apply suction through the working channel to vacuum debris from the target surgical site through the working channel.

16. A method for removing debris from a target surgical site, comprising:
inserting a distal portion of a scope assembly into a bodily lumen, the distal portion of the scope assembly including:
an elongated shaft including a working channel, the working channel being open at a distal end of the elongated shaft, the elongated shaft being configured to be inserted through the bodily lumen to the target surgical site;
an external member extending from a proximal end to a distal end and configured to be coupled to the elongated shaft, the external member comprising a proximal hub and a tube extending distally from the hub and defining a first external channel therein;
a coupling mechanism configured to couple the distal end of the external member to the distal end of the elongated shaft, the coupling mechanism including a first lumen a proximal portion of which is sized and shaped to be inserted into a distal portion of the elongated shaft such that the first lumen is open to the working channel and wherein a second lumen of the coupling mechanism is sized and shaped to receive the distal end of the external member; and
an end cap coupled to the distal end of the elongated shaft, the end cap including an end cap channel extending therethrough such that, when the end cap is coupled to the elongated shaft, the end cap channel is open to the working channel;
inserting a medical device through the first external channel until a distal end of the medical device enters the target surgical site, the medical device configured to break up debris within the target surgical site; and
vacuuming the debris from the target surgical site through the working channel via a vacuum pump fluidly connected to the elongated shaft.

17. The method of claim 16, further comprising:
inserting a guide wire into the bodily lumen to the target surgical site; and
guiding the distal portion of the scope assembly, via the guide wire, to the target surgical site.

18. The method of claim 16, wherein the medical device is a laser fiber assembly, the laser fiber assembly including a valve seal at a proximal end thereof configured to mate with a proximal end of the hub, sealing the laser fiber assembly to the scope assembly.

19. The method of claim 16, wherein the scope assembly further comprises a clip configured to couple the first external channel to a proximal portion of the elongated shaft, the clip including first and second slotted channels, each of the first and second slotted channels configured to receive one of the first external channel and the elongated shaft therethrough.

20. The method of claim 16, further comprising injecting fluid through the first external channel via a fluid source to flush out the target surgical site.

\* \* \* \* \*